(12) United States Patent
Liu et al.

(10) Patent No.: US 8,288,580 B2
(45) Date of Patent: Oct. 16, 2012

(54) BENZOPHENONE COMPOUND

(75) Inventors: Jimmy Liu, Zhonghe (TW); Kuei-Ta Chen, Zhonghe (TW); I-Ling Chen, Zhonghe (TW)

(73) Assignee: Double Bond Chemical Ind. Co., Ltd., Taipei County (TW)

( * ) Notice: Subject to any disclaimer, the term of this patent is extended or adjusted under 35 U.S.C. 154(b) by 205 days.

(21) Appl. No.: 12/942,832

(22) Filed: Nov. 9, 2010

(65) Prior Publication Data
US 2011/0282091 A1 Nov. 17, 2011

(30) Foreign Application Priority Data

May 13, 2010 (TW) .............................. 99115282 A

(51) Int. Cl.
*C07C 69/78* (2006.01)
(52) U.S. Cl. ................. 560/52; 560/53; 560/54
(58) Field of Classification Search .............. 560/52, 560/53, 54
See application file for complete search history.

(56) References Cited

U.S. PATENT DOCUMENTS

| | | | | |
|---|---|---|---|---|
| 3,574,617 | A * | 4/1971 | Skoultchi .............. | 430/281.1 |
| 6,031,051 | A * | 2/2000 | Wu ........................ | 525/243 |
| 7,838,110 | B2 * | 11/2010 | Zhu et al. ............... | 428/345 |
| 2011/0224324 | A1 * | 9/2011 | Loccufier et al. ....... | 522/34 |

FOREIGN PATENT DOCUMENTS
WO    WO96/33156    * 10/1996
* cited by examiner

Primary Examiner — Sikarl Witherspoon
(74) Attorney, Agent, or Firm — Frommer Lawrence & Haug LLP; Ronald R. Santucci

(57) ABSTRACT

A benzophenone compound is represented by the following formula (I):

$$(A)_n\text{-}X\text{—}(B)_m \quad\quad (I)$$

wherein
X is an organic moiety having (n+m) valence, (n+m) being an integer ranging from 1 to 4;
A is

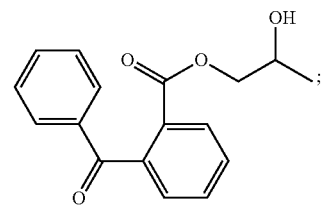

B is

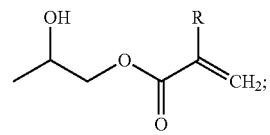

R is H or a methyl group;
n is the number of A bonded to X and is an integer ranging from 1 to 4; and
m is the number of B bonded to X and is an integer ranging from 0 to 3.

14 Claims, No Drawings

BENZOPHENONE COMPOUND

CROSS-REFERENCE TO RELATED APPLICATION

This application claims priority of Taiwanese application no. 099115282, filed on May 13, 2010, the disclosure of which is incorporated herein by reference.

BACKGROUND OF THE INVENTION

1. Field of the Invention

This invention relates to a benzophenone compound suitable for use as a photosensitizer.

2. Description of the Related Art

Benzophenone derivatives are commonly used as a photosensitizer or a photoinitiator for facilitating curing of an ultraviolet (UV) curable resin or ink. However, when a conventional benzophenone derivative with small molecular weight is used with a UV curable ink for preparation of a package for foodstuffs, the problems of relatively strong bad odor for the package and migration of the benzophenone derivative from the cured polymer to a surface of the package are likely to occur.

In order to overcome the abovementioned problems, many researches have focused on the preparation of a photosensitizer (or a photoinitiator) having high molecular weights, for example, a polymeric photosensitizer (or photoinitiator).

JP S57-109804 (A) discloses a UV curable composition which is used as a polymeric initiator and is represented by the following formula:

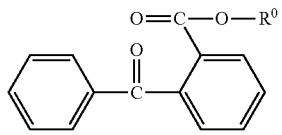

wherein $R^0$ is a $C_{3-10}$ alkenyl group or a phenyl group substituted with one or two $C_{3-10}$ alkenyl groups. However, in this patent, the problems of bad odor and migration of the benzophenone compound still occur.

WO 96/33156 discloses a benzophenone compound represented by the following formula:

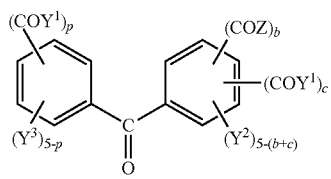

wherein each of Z and $Y^1$ independently represents an alkylene polyol moiety or a polyalkylene polyol moiety; each of $Y^2$ and $Y^3$ is a univalent group; b ranges from 1 to 5; c ranges from 0 to 4; and p ranges from 0 to 5. When the benzophenone compound of this WO patent is used in a UV curable ink, a relatively large amount of the benzophenone compound and a relatively long time for curing are required. In addition, bad odor is still a problem for the WO patent.

SUMMARY OF THE INVENTION

Therefore, an object of the present invention is to provide a benzophenone compound suitable for use as a photosensitizer for a UV curable ink that can overcome the aforesaid drawbacks associated with the prior art.

Accordingly, a benzophenone compound of the present invention is represented by the following formula (I):

wherein

X is an organic moiety having (n+m) valence, (n+m) being an integer ranging from 1 to 4;

A is

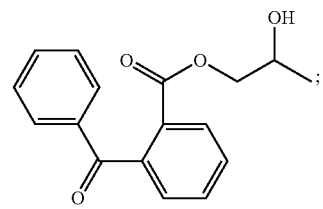

B is

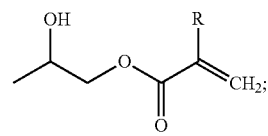

R is H or a methyl group;

n is the number of A bonded to X and is an integer ranging from 1 to 4; and m is the number of B bonded to X and is an integer ranging from 0 to 3.

DETAILED DESCRIPTION OF THE PREFERRED EMBODIMENTS

A benzophenone compound of the present invention is represented by the following formula (I):

wherein

X is an organic moiety having (n+m) valence, (n+m) being an integer ranging from 1 to 4;

A is

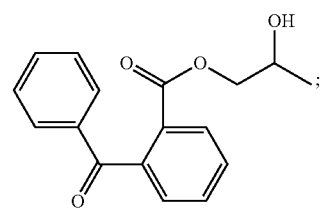

B is

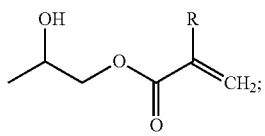

R is H or a methyl group;

n is the number of A bonded to X and is an integer ranging from 1 to 4; and m is the number of B bonded to X and is an integer ranging from 0 to 3.

In particular, X is an organic moiety that can be deemed as an epoxy resin without the epoxy group on the main chain.

Preferably, X is a polyester or heterocyclic group. When X is a univalent group, (n+m) is 1 (i.e., n is 1 and m is 0). Preferably, X is Ar—O—CH$_2$— or

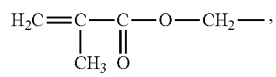

and Ar is a phenyl group optionally substituted with an alkyl group or halogen. Examples of Ar include, but are not limited to, a phenyl group, a 2-methylphenyl group, a 4-methylphenyl group, etc.

When X is a divalent group, (n+m) is 2 (i.e., n is 1 and m is 1, or n is 2 and m is 0). Preferably, X is

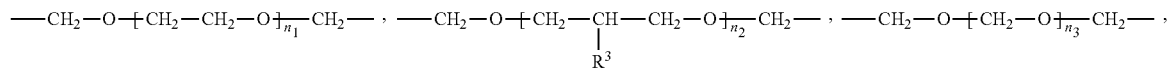

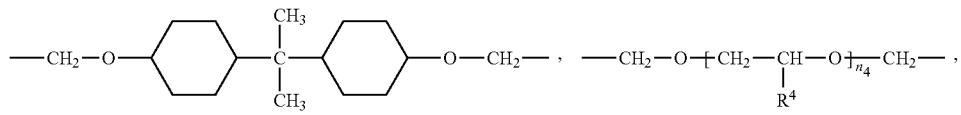

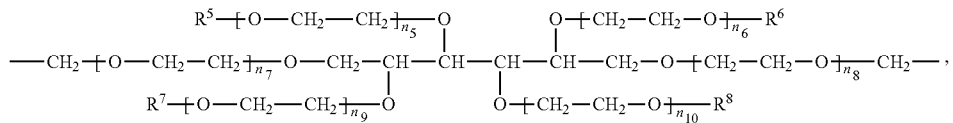

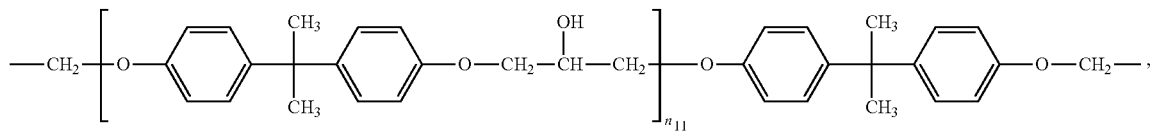

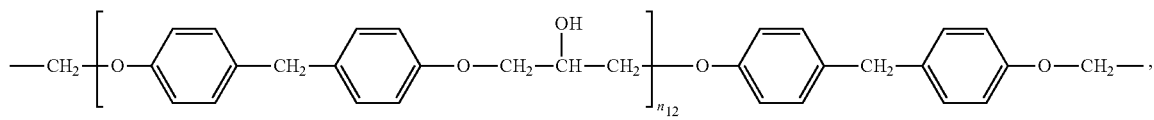

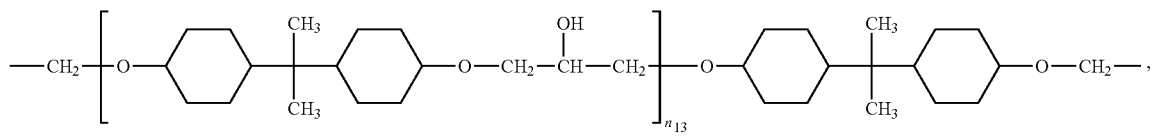

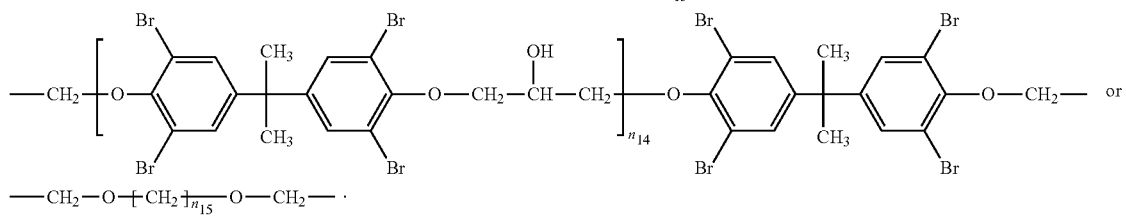

$R^3$ is hydrogen or an alkyl group. $R^4$ is an alkyl group. $R^5$, $R^6$, $R^7$ and $R^8$ are independently hydrogen, an alkyl group or
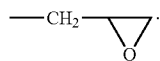
$n_1$, $n_2$, $n_3$ and $n_4$ independently range from 4 to 10. $n_5$, $n_6$, $n_7$, $n_8$, $n_9$, $n_{10}$, $n_{11}$, $n_{12}$, $n_{13}$ and $n_{14}$ independently range from 0 to 2. $n_{15}$ ranges from 4 to 6.
When X is a trivalent group, (n+m) is 3 (e.g., n is or n is 2 and m is 1). Preferably, X is
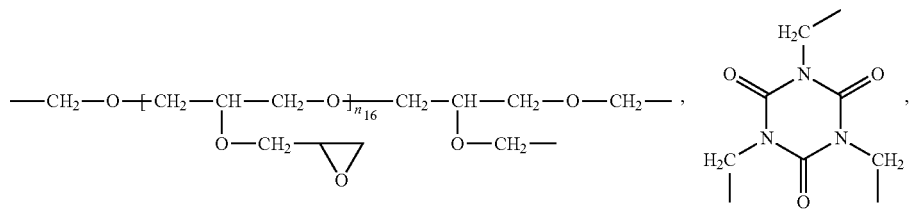
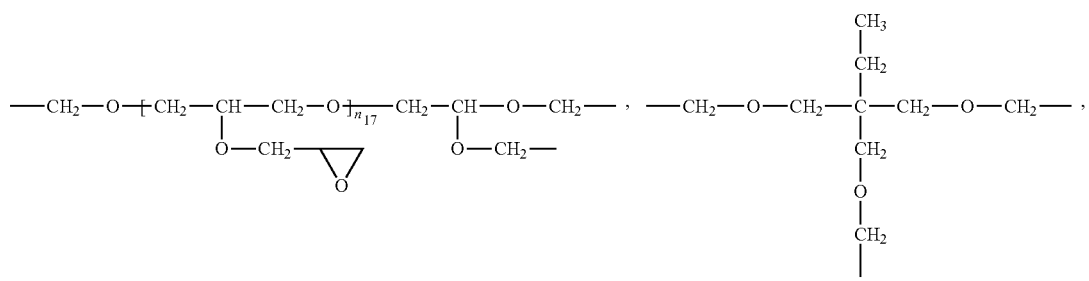
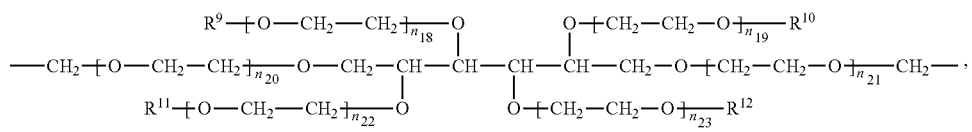
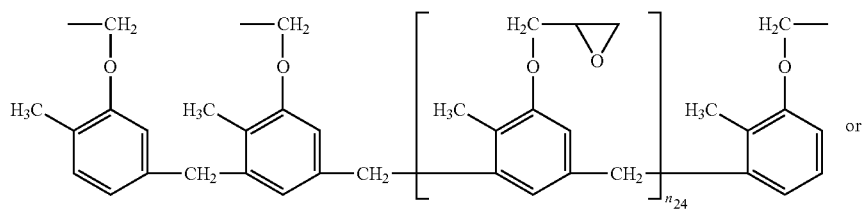
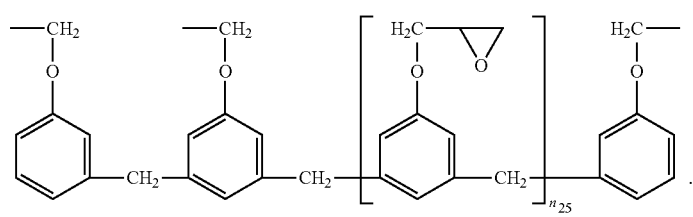

One of $R^9$, $R^{10}$, $R^{11}$ and $R^{12}$ is a methylene group, and the others are independently hydrogen, an alkyl group or
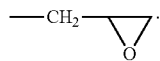
$n_{16}$, $n_{17}$, $n_{18}$, $n_{19}$, $n_{20}$, $n_{21}$, $n_{22}$, $n_{23}$, $n_{24}$ and $n_{25}$ independently range from 0 to 4.
When X is a tetravalent group, (n+m) is 4 (e.g., n is 4, n is 3 and m is 1, or n is 2 and m is 2). Preferably, X is
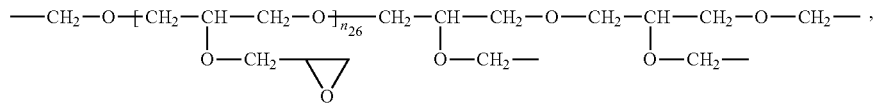
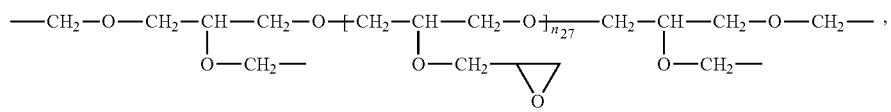
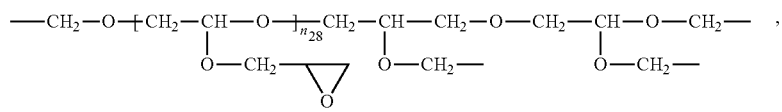
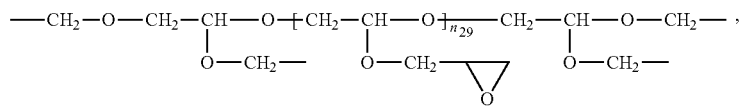
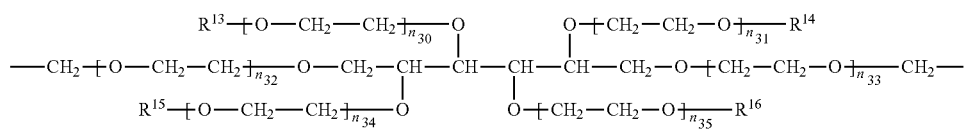
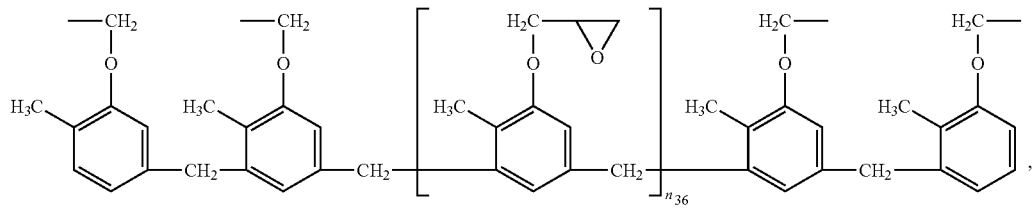
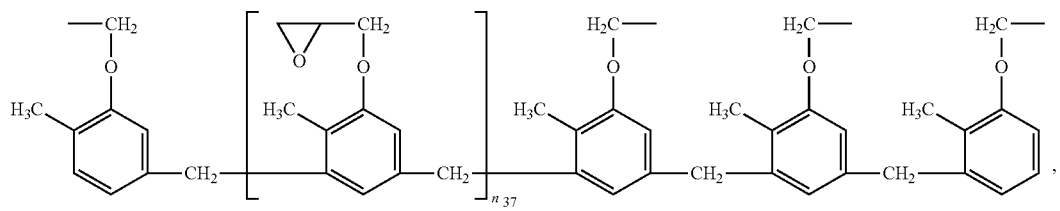
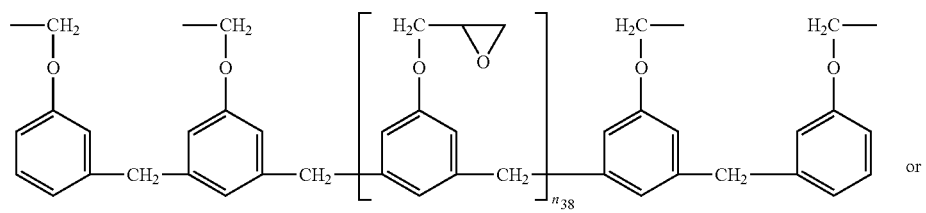
or

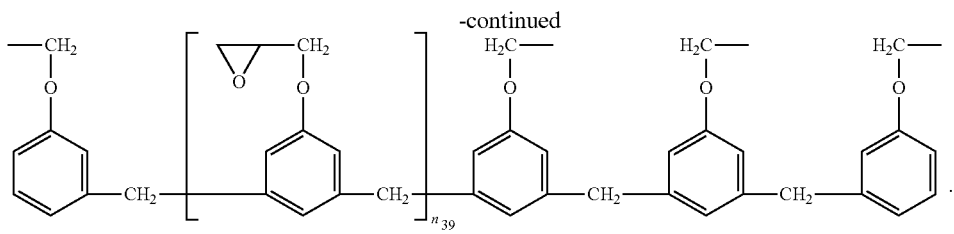

Two of $R^{13}$, $R^{14}$, $R^{15}$ and $R^{16}$ are methylene groups, the other two are independently hydrogen, alkyl groups, or

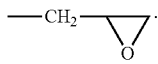

$n_{26}$, $n_{27}$, $n_{28}$, $n_{29}$, $n_{30}$, $n_{31}$, $n_{32}$, $n_{33}$, $n_{34}$, $n_{35}$, $n_{36}$, $n_{37}$, $n_{38}$ and $n_{39}$ independently range from 0 to 4.

The benzophenone compound of this invention is synthesized by reacting 2-benzoylbenzoic acid, an epoxy resin, and an optional acrylic compound. The reaction for synthesizing the benzophenone compound of this invention is shown below:

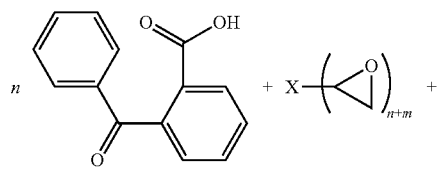

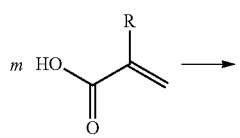

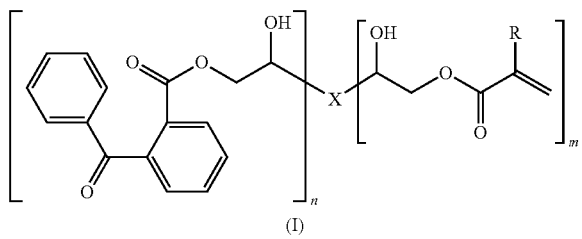

(I)

X, R, n and m are the same as those defined above.

The optional acrylic compound will provide acrylic group for the benzophenone compound of the present invention. The acrylic group in the benzophenone compound can also react with the resin or monomers of the UV curable ink, thereby preventing the benzophenone compound from migration.

Preferably, in the reaction for synthesizing the benzophenone compound of this invention, hydroquinone monomethyl ether (MEHQ) or triphenyl phosphine (TPP) may also be added. MEHQ is used to prevent the double bond(s) of the benzophenone compound in the UV curable ink from self-crosslinking, and TPP is used as a catalyst.

Preferably, the reaction is conducted at a temperature ranging from 100° C. to 120° C. In the examples of this invention, the reaction is conducted at 110° C.

It should be noted that, the benzophenone group of the benzophenone compound will produce free radicals when irradiated with light, and the free radicals will react with the resin or monomers of the UV curable ink. Thus, the reaction between the benzophenone compound and the ink can be controlled by the number of the benzophenone group. Moreover, the molecular weight of the benzophenone compound used as a photosensitizer may be increased by increasing the number of the benzophenone group, thereby preventing the migration of the benzophenone compound.

The present invention is explained in more detail below by way of the following examples. It should be noted that the examples are only for illustration and are not for limiting the scope of the present invention.

EXAMPLES

Example 1

To a mixture containing 1.0 mole (226.2 g) of 2-benzoylbenzoic acid and 1.0 mole (230.31 g) of an epoxy resin represented by the following formula (1) was added TPP (9000 ppm). Then, the mixture was reacted at 110° C. until an acid value of the 2-benzoylbenzoic acid was no longer decreased (about 8 hrs). A benzophenone compound represented by the following formula (1) was obtained.

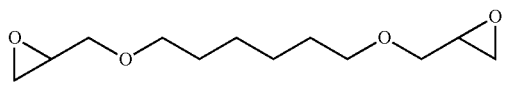
(i)
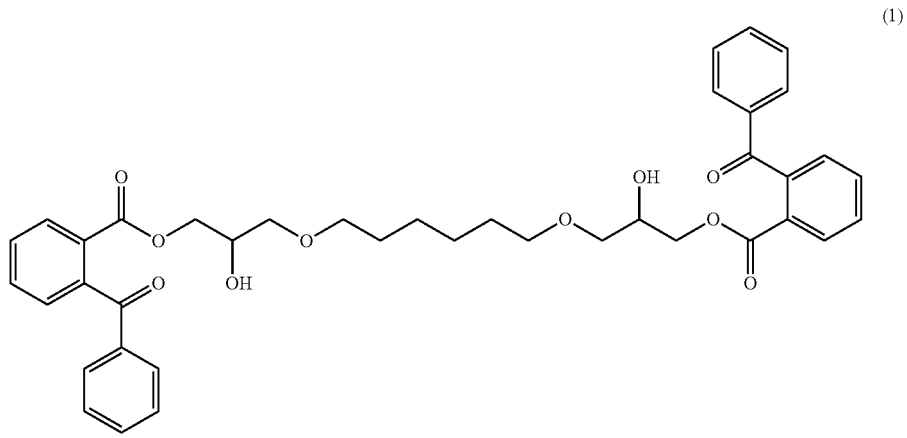
(1)
Structure identification: Anal. calcd for $C_{40}H_{42}O_{10}$ (molecular weight: 682.77): C 70.37%; H 6.20%; O 23.43%.
Example 2
The process for preparing the benzophenone compound in Example 2 is similar to that of Example 1, except that, in this example, the epoxy resin having the following formula (ii) was used. A benzophenone compound thus obtained has the following formula (2).
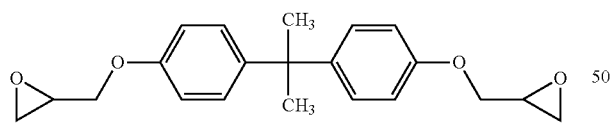
(ii)
-continued
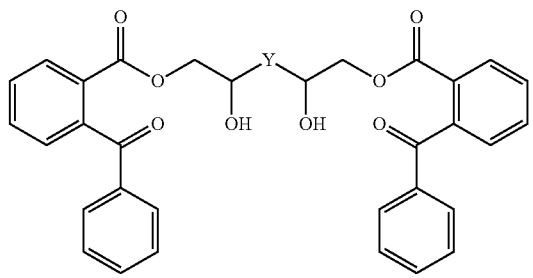
(2)
Wherein:
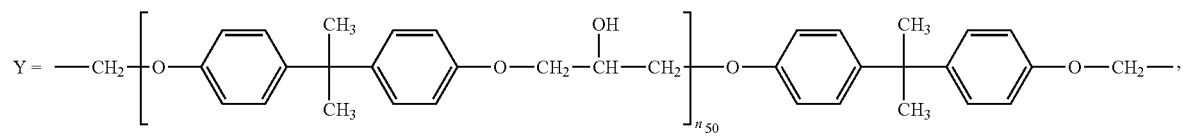

$n_{50}$ is 0.1, and is calculated based an epoxy equivalence of the epoxy resin.

Structure identification: Anal. calcd for $C_{49}H_{44}O_{10}$ $(C_{18}H_{20}O_3)_{0.1}$ (molecular weight: 792.89+284.36×0.1): C 74.7%; H 5.99%; O 19.31%.

Example 3

The process for preparing the benzophenone compound in Example 3 is similar to that of Example 1, except that, in this example, the epoxy resin having the following formula (iii) was used. A benzophenone compound having the following formula (3) was obtained.

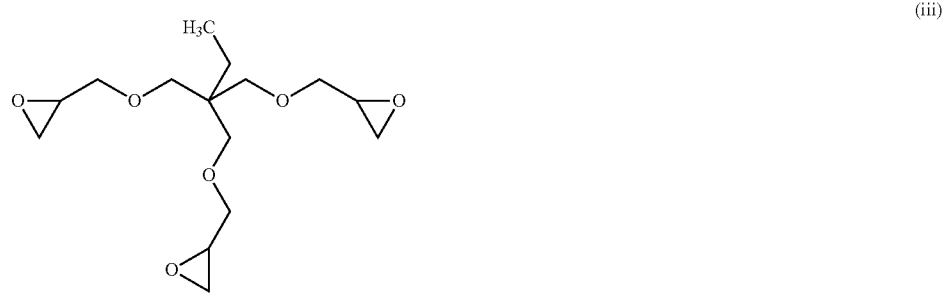

(iii)

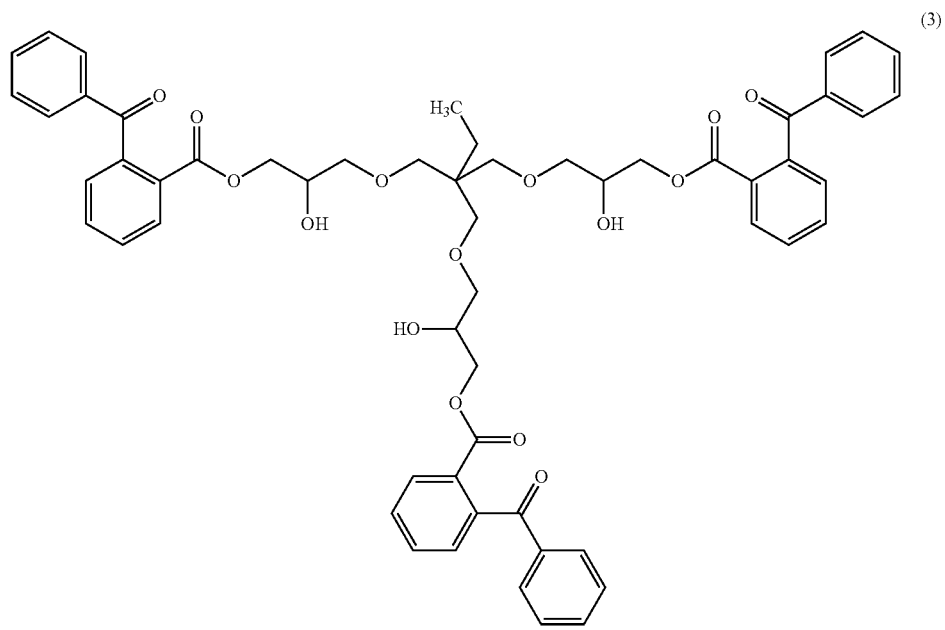

(3)

Structure identification: Anal. calcd for $C_{57}H_{56}O_{15}$ (molecular weight: 981.07): C 69.78%; H 5.75%; O 24.46%.

Example 4

The process for preparing the benzophenone compound in Example 4 is similar to that of Example 1, except that, in this example, the epoxy resin having the following formula (Iv) was used. A benzophenone compound having the following formula (4) was obtained.

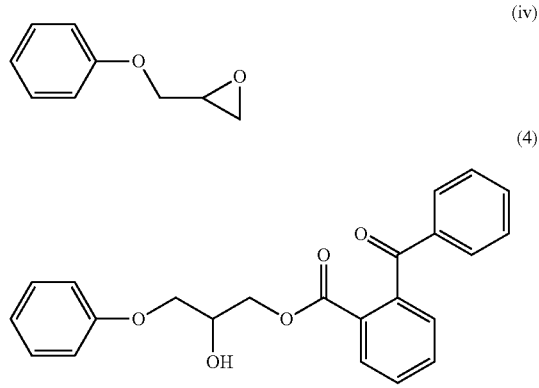

Structure identification: Anal. calcd for $C_{23}H_{20}O_{15}$ (molecular weight: 376.4): C 73.39%; H 5.36; O 21.25%.

Example 5

To a mixture containing 0.5 mole (113.1 g) of 2-benzoylbenzoic acid, 0.5 mole (36.0 g) of acrylic acid, and 1.0 mole (189.0 g) of an epoxy resin represented by the above-mentioned formula (ii) was added TPP (9000 ppm). Then, the mixture was reacted at 110° C. until an acid value of the 2-benzoylbenzoic acid was no longer decreased (about 8 hrs). A benzophenone compound represented by the following formula (5) was obtained.

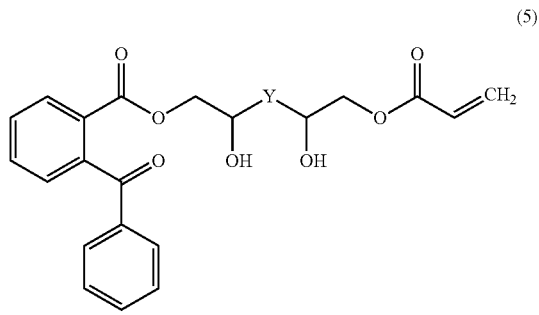

Wherein:

$n_{50}$ is 0.1, and is calculated based an epoxy equivalence of the epoxy resin.

Structure identification: Anal. calcd for $C_{38}H_{38}O_9$ $(C_{18}H_{20}O_3)_{0.1}$ (molecular weight: 638.72+284.36×0.1): C 71.46%; H 6.00%; O 22.54%.

[Migration Test]

Each of the benzophenone compounds of Examples 1 to 5 of this invention and methyl o-benzoylbenzoate, that is a commercially available photosensitizer and that is used as a comparative example in this invention, were subjected to a migration test.

3 g of tripropyl glycol diacrylate (TPGDA) and 0.8 g of the benzophenone compound were sequentially added into 7 g of bisphenol A epoxy diacrylate, followed by stirring completely so as to obtain a coating material. Thereafter, the coating material was coated on a polyethylene terephthalate film (PET film, 10 cm×10 cm) to a thickness of about 40 µm, and then was cured by a UV light to obtain a specimen. The specimen was then dipped in an ethanol solution (5%) for 120 hours, followed by concentrating the ethanol solution after removing the specimen. The amount of each of the benzophenone compounds of Examples 1 to 5 of this invention and methyl o-benzoylbenzoate contained in the respective one of the ethanol solutions was determined by HPLC. The results are shown in Table 1.

TABLE 1

| Specimens | Amount of the compound (ppm) |
|---|---|
| Comparative Example | 179 |
| Example 1 | 12 |
| Example 2 | 14 |
| Example 3 | 9 |
| Example 4 | 48 |
| Example 5 | 8 |

As shown in Table 1, compared to the commercially available photosensitizer, the migration situation for the benzophenone compounds of the examples of the present invention is effectively diminished, and thus, the same is suitable for use as a good photosensitizer (or photoinitiator) in a polymerization process.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

What is claimed is:

1. A benzophenone compound represented by the following formula (1):

$$(A)_n\text{-}X\text{---}(B)_m \qquad (I)$$

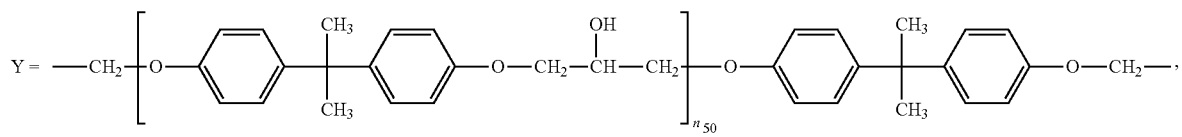

wherein

X is an organic moiety having (n+m) valence, (n+m) being an integer ranging from 1 to 4;

A is

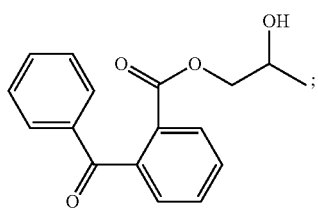

B is

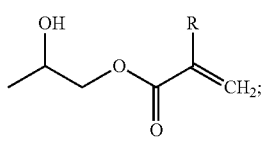

R is H or a methyl group;

n is the number of A bonded to X and is an integer ranging from 1 to 4; and m is the number of B bonded to X and is an integer ranging from 0 to 3.

2. The benzophenone compound of claim 1, wherein X is a polyester or heterocyclic group.

3. The benzophenone compound of claim 1, wherein n is 1, m is 0, and X is a univalent group.

4. The benzophenone compound of claim 3, wherein X is Ar—O—CH$_2$— or $$H_2C=C(CH_3)-C(=O)-O-CH_2-,$$

Ar being a phenyl group optionally substituted with an alkyl group or halogen.

5. The benzophenone compound of claim 1, wherein X is a divalent group.

6. The benzophenone compound of claim 5, wherein X is

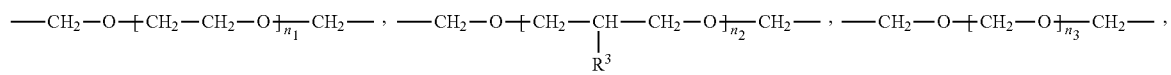

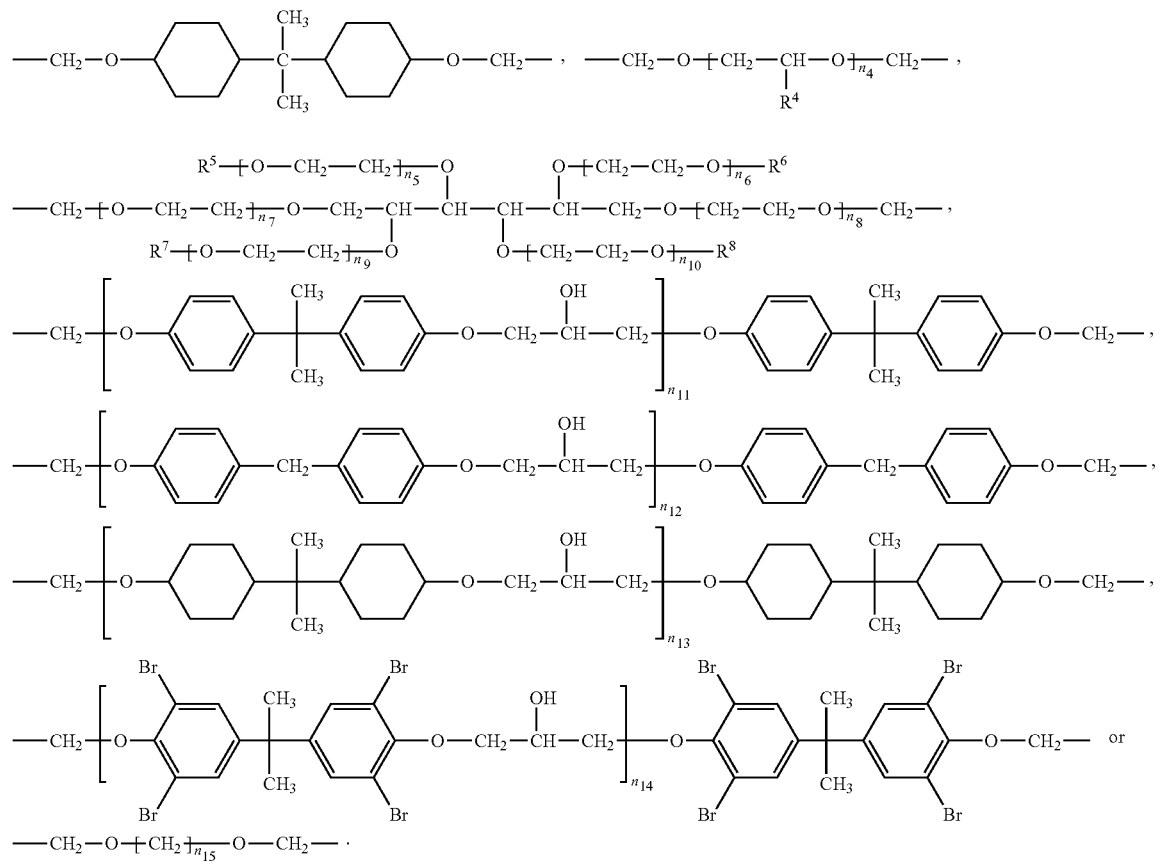

$R^3$ being hydrogen or an alkyl group, $R^4$ being an alkyl group, $R^5$, $R^6$, $R^7$ and $R^8$ being independently hydrogen, an alkyl group or

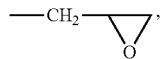

$n_1$, $n_2$, $n_3$ and $n_4$ independently ranging from 4 to 10, $n_5$, $n_6$, $n_7$, $n_8$, $n_9$, $n_{10}$, $n_{11}$, $n_{12}$, $n_{13}$ and $n_{14}$ independently ranging from 0 to 2, and $n_{15}$ ranging from 4 to 6.

7. The benzophenone compound of claim 6, wherein n is 1 and m is 1.

8. The benzophenone compound of claim 6, wherein n is 2 and m is 0.

9. The benzophenone compound of claim 1, wherein n is 2, m is 1, and X is a trivalent group.

10. The benzophenone compound of claim 9, wherein X is

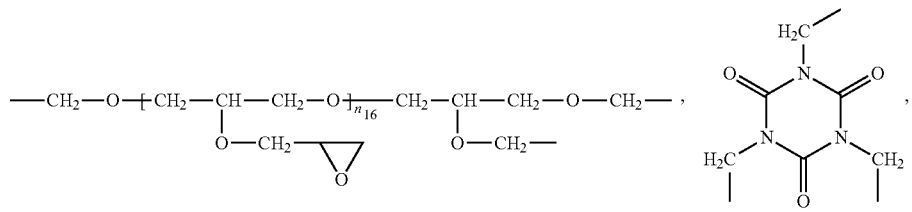

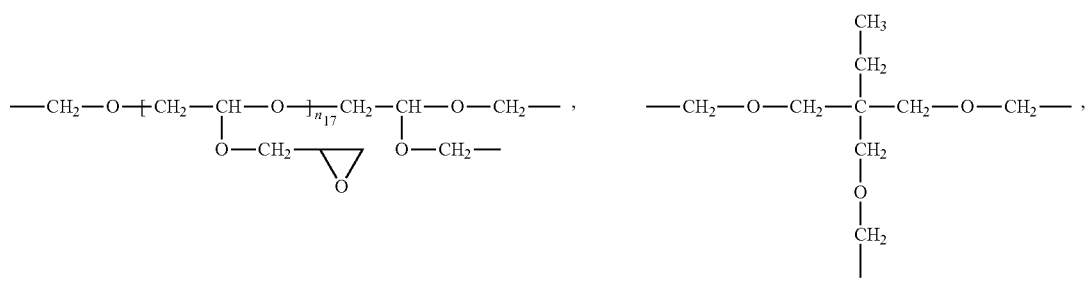

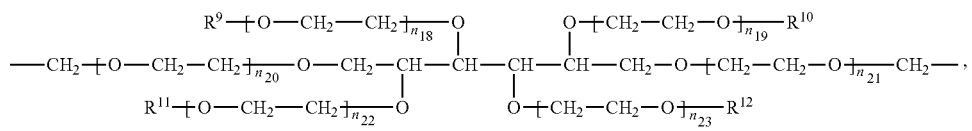

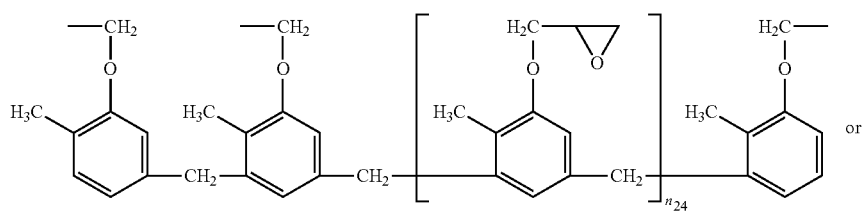

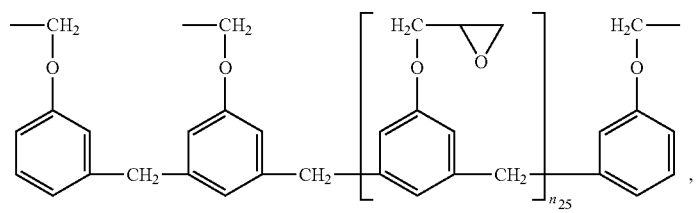

one of $R^9$, $R^{10}$, $R^{11}$ and $R^{12}$ being a methylene group, the other three being independently hydrogen, an alkyl group or
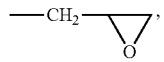,
$n_{16}$, $n_{17}$, $n_{18}$, $n_{19}$, $n_{20}$, $n_{21}$, $n_{22}$, $n_{23}$, $n_{24}$ and $n_{25}$ independently ranging from 0 to 4.
11. The benzophenone compound of claim 1, wherein X is a tetravalent group.
12. The benzophenone compound of claim 11, wherein X is
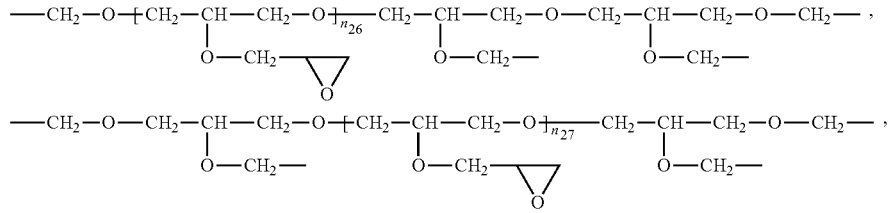
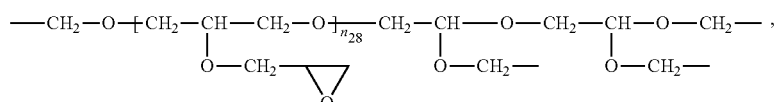
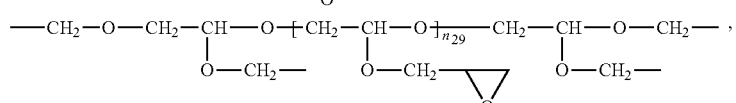
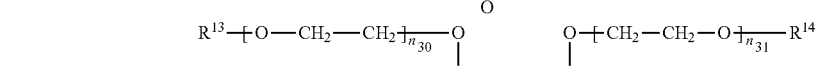
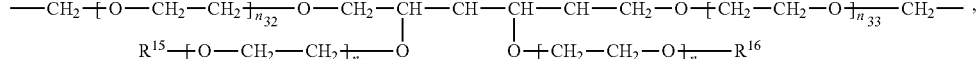
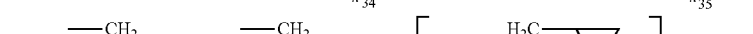
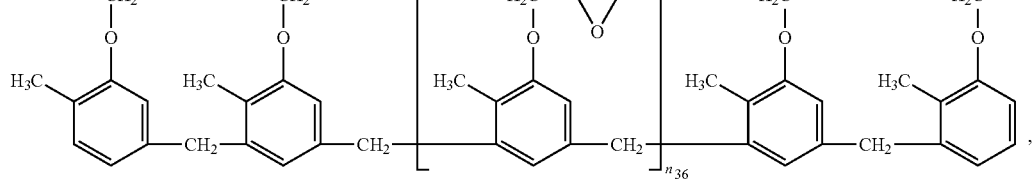
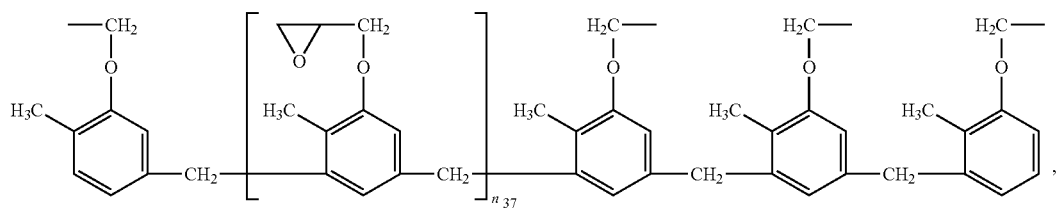
or
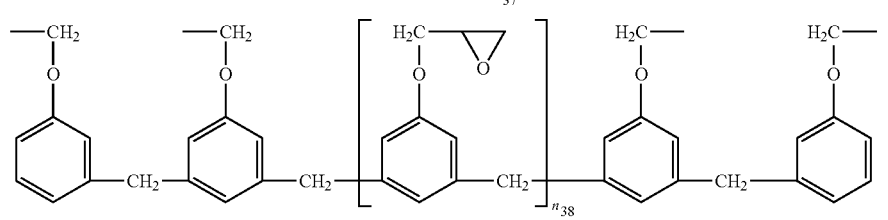, two of $R^{13}$, $R^{14}$, $R^{15}$ and $R^{16}$ being a methylene group, the other two being independently hydrogen, an alkyl group, or
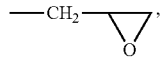
$n_{26}$, $n_{27}$, $n_{28}$, $n_{29}$, $n_{30}$, $n_{31}$, $n_{32}$, $n_{33}$, $n_{34}$, $n_{35}$, $n_{36}$, $n_{37}$, $n_{38}$ and $n_{39}$ independently ranging from 0 to 4.
13. The benzophenone compound of claim 11, wherein n is 3 and m is 1.
14. The benzophenone compound of claim 11, wherein n is 2 and m is 2.
* * * * *